(12) United States Patent
Dubief et al.

(10) Patent No.: US 6,511,671 B1
(45) Date of Patent: *Jan. 28, 2003

(54) DETERGENT COSMETIC COMPOSITION COMPRISING A SILICONE AND AN AMPHOTERIC POLYMER WITH FATTY CHAINS AND USE

(75) Inventors: Claude Dubief, Les Chesnay (FR); Serge Restle, Saint-Prix (FR); Géraldine Fack, Levallois (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/599,831

(22) Filed: Jun. 23, 2000

(30) Foreign Application Priority Data

Jun. 25, 1999 (FR) .............................. 99 08170

(51) Int. Cl.$^7$ ........................... A61K 7/06; A61K 7/075; A61K 7/00; A61K 7/08; A61K 35/36
(52) U.S. Cl. ................. 424/401; 424/70.17; 424/70.12; 514/881; 510/122; 510/123; 510/124
(58) Field of Search .............................. 424/401, 70.17, 424/70.12; 510/122–124; 514/881

(56) References Cited

U.S. PATENT DOCUMENTS

| | | |
|---|---|---|
| 2,528,378 A | 10/1950 | Mannheimer |
| 2,781,354 A | 2/1957 | Mannheimer |
| 4,217,914 A | 8/1980 | Jacquet et al. |
| 4,240,450 A | 12/1980 | Grollier et al. |
| 4,839,166 A | 6/1989 | Grollier et al. |
| 4,938,950 A | 7/1990 | Lang et al. |
| 4,996,059 A | 2/1991 | Grollier et al. |
| 5,089,252 A | 2/1992 | Grollier et al. |
| 5,439,673 A * | 8/1995 | Murray .................... 424/70.12 |

FOREIGN PATENT DOCUMENTS

| | | |
|---|---|---|
| EP | 0 272 472 | 6/1988 |
| EP | 0 337 354 | 10/1989 |
| FR | 2 270 846 | 12/1975 |
| FR | 2 383 660 | 10/1978 |
| FR | 2 470 596 | 6/1981 |
| FR | 2 519 863 | 7/1983 |
| FR | 2 598 611 | 11/1987 |
| FR | 2 779 642 | 12/1999 |
| GB | 0432951 A2 * | 6/1991 |
| JP | 090887721 A * | 3/1994 |
| WO | WO 98/44012 | 10/1998 |
| WO | WO 99/13842 | 3/1999 |

OTHER PUBLICATIONS

Derwent Accession No.: 1994–140934, JP 06087721 A, KAO Corp, Hair Cosmetic Material Having Good Conditioning and Hairdressing effects . . . , See: abstract.*
M.R. Porter, "Handbook of Surfactants", Blackie & Son Ltd., Glasgow & London, 1991, pp. 166–178.
Derwent Publication Ltd., London, GB; Class A96, AN 1994–140934, XP002135709, JP 06 87721, Mar. 29, 1994.
English language Derwent Abstract of FR 2 779 642. (No date).

* cited by examiner

*Primary Examiner*—Frederick Krass
*Assistant Examiner*—Clinton Ostrup
(74) *Attorney, Agent, or Firm*—Finnegan, Henderson, Farabow, Garrett & Dunner, LLP

(57) ABSTRACT

Detergent composition comprising, in a cosmetically acceptable medium, at least one washing base, at least one water-insoluble silicone and at least one amphoteric polymer comprising from 1 to 20 mol % of at least one monomeric unit chosen from (meth)acrylate and (meth)acrylamide types having at least one fatty chain, the fatty chain having from 8 to 30 carbon atoms. These compositions may possess improved cosmetic properties, in particular the sleeking of the hair. The compositions can be used for cleaning, care and styling of the hair.

25 Claims, No Drawings

DETERGENT COSMETIC COMPOSITION COMPRISING A SILICONE AND AN AMPHOTERIC POLYMER WITH FATTY CHAINS AND USE

The present invention relates to cosmetic compositions with improved properties, preferably intended simultaneously for cleaning, conditioning and styling the hair and comprising, in a cosmetically acceptable carrier, at least one washing base chosen from surfactants with detergent power, at least one water-insoluble silicone, and at least one amphoteric polymer comprising from 1 to 20 mol % of at least one monomeric unit chosen from (meth)acrylate and (meth) acrylamide types containing at least one fatty chain, the fatty chain containing from 8 to 30 carbon atoms. The invention also relates to the use of the compositions in the above-mentioned cosmetic application.

The use of detergent hair compositions (or shampoos) based essentially on conventional surfactants especially of the anionic, nonionic and/or amphoteric type, but more particularly of the anionic type, is common for cleaning and/or washing the hair. These compositions are applied to wet hair and the foam generated by massaging or rubbing with the hands allows, after rinsing with water, the removal of the various types of dirt initially present on the hair.

These base compositions indeed possess good washing power, but the intrinsic cosmetic properties attached to them may remain nevertheless fairly weak, in particular because of the fact that the relatively aggressive nature of such a cleaning treatment can cause in the long term damage to the hair fiber which is marked to a greater or lesser degree, and may be linked in particular to the gradual removal of the lipids or proteins contained in or at the surface thereof.

Consequently, to improve the cosmetic properties of the above detergent compositions, and more particularly of those which are intended to be applied to sensitive hair (i.e., hair which has become damaged or which has been made fragile, especially under the chemical action of atmospheric agents and/or of hair treatments, such as permanent waving, dyeing or bleaching) it is now customary to introduce therein additional cosmetic agents called conditioning agents, intended mainly to repair or limit the harmful or undesirable effects induced by the various treatments or attacks to which the hair fibers are subjected more or less repeatedly. These conditioning agents can of course also improve the cosmetic behavior of natural hair.

The conditioning agents most commonly used to date in shampoos are silicones, which indeed confer on washed, dry or wet hair greatly improved ease of disentanglement, softness and sleekness compared to what may be obtained with the corresponding cleaning compositions not containing them.

However, and in spite of the progress recently made in the field of shampoos, the latter are not completely satisfactory, such that a high demand currently still exists in relation to being able to have products exhibiting better performance at the level of one or more of the cosmetic properties mentioned above.

The present invention is aimed at satisfying such a need.

Thus, following major research studies carried out on subjects, it has now been found completely unexpectedly and surprisingly, that by introducing at least one amphoteric polymer comprising from 1 to 20 mol % of at least one monomeric unit chosen from (meth)acrylate and (meth) acrylamide types containing at least one fatty chain, the fatty chain containing from 8 to 30 carbon atoms, into detergent compositions containing at least one washing base, in particular hair, the compositions also containing at least one water-insoluble silicone, it is possible to substantially and significantly improve the cosmetic properties attached thereto, while preserving their good intrinsic washing power.

Without wishing to limit the present invention to any theory, it would appear that, during rinsing, particular interactions and/or affinities exist between the silicones, the amphoteric polymers in accordance with the invention and the hair which promote a uniform, substantial and lasting deposition of the silicones and amphoteric polymers at the surface of the hair. This qualitative and quantitative deposition is probably one of the causes of the improvement observed in the final properties in highly preferred embodiments, in particular the ease of hairstyling, the shape retention, the vitality and the body of the treated hair.

All these discoveries form the basis of the present invention.

Thus, according to the present invention, novel, in particular detergent and in particular hair, compositions are now provided comprising, in a cosmetically acceptable medium, at least one washing base, at least one water-insoluble silicone and at least one amphoteric polymer comprising from 1 to 20 mol % of at least one monomeric unit chosen from (meth)acrylate and (meth)acrylamide types containing at least one fatty chain, the fatty chain containing from 8 to 30 carbon atoms.

The subject of the invention is also the cosmetic use of the above compositions for cleaning, conditioning and styling the hair.

However, other characteristics, aspects and advantages of the invention will appear even more clearly on reading the description which follows as well as the concrete, but not at all limiting, examples intended to illustrate it.

An aspect of the invention involves hair product compositions comprising (i) at least one surfactant with detergent power intended to form the washing base, (ii) at least one water-insoluble silicone and (iii) at least one of the amphoteric polymers referred to above.

A—Washing Base

The compositions in accordance with the invention comprise at least one washing base, generally aqueous.

The surfactant(s) forming the washing base may equally well be chosen, alone or as mixtures, from anionic, amphoteric, nonionic, zwitterionic and cationic surfactants. However, according to the invention, the washing base preferably comprises anionic surfactants or mixtures of anionic surfactants and amphoteric surfactants or nonionic surfactants.

The minimum quantity of washing base is that which is just sufficient to confer a satisfactory foaming and/or detergent power on the final composition, and excessively large quantities of washing base do not necessarily provide additional advantages.

Thus, according to the invention, the washing base may be present in an amount generally ranging from 4% to 50% by weight, preferably from 6% to 25% by weight, and still more preferably from 8% to 20% by weight, of the total weight of the final composition.

The surfactants which are suitable for carrying out the present invention are in particular the following:

(i) Anionic Surfactant(s)

By way of example of anionic surfactants which can be used, alone or as mixtures, in the context of the present invention there may be mentioned in particular (nonlimiting list) the salts (in particular alkali metal, especially sodium, salts, ammonium salts, amine salts, amino alcohol salts or magnesium salts) of the following compounds: alkyl sulphates, alkyl ether sulphates, alkylamidoether sulphates, alkylarylpolyether sulphates, monoglyceride sulphates; alkyl sulphonates, alkyl phosphates, alkylamidesulphonates, alkyl aryl sulphonates, -olefinsulphonates, paraffinsulphonates; ($C_6$–$C_{24}$)alkyl sulphosuccinates, ($C_{6-C24}$)alkyl ether sulphosuccinates, ($C_6$–$C_{24}$)alkylamide sulphosuccinates; ($C_6$–$C_{24}$)alkyl sulphoacetates; ($C_6$–$C_{24}$)acyl sarcosinates and ($C_6$–$C_{24}$)acyl glutamates. It is also possible to use ($C_6$–$C_{24}$)alkyl polyglycoside carboxylic esters such as alkyl glucoside citrates, alkyl polyglycoside tartrate and alkyl polyglycoside sulphosuccinates, alkyl sulphosuccinamates; acyl isethionates and N-acyltaurates. The alkyl or acyl radical of all these various compounds preferably comprises from 12 to 20 carbon atoms, and the aryl radical preferably is a phenyl or benzyl group. Among the anionic surfactants which can still be used, there may also be mentioned the salts of fatty acids such as the salts of oleic, ricinoleic, palmitic and stearic acids, the acids of copra oil or of hydrogenated copra oil; the acyl lactylates whose acyl radical comprises 8 to 20 carbon atoms. It is also possible to use the alkyl D-galactosiduronic acids and their salts, the polyoxyalkylenated ($C_6$–$C_{24}$)alkyl ether carboxylic acids, the polyoxyalkylenated ($C_6$–$C_{24}$)alkylaryl ether carboxylic acids, the polyoxyalkylenated ($C_6$–$C_{24}$) alkylamido ether carboxylic acids and salts thereof, in particular those comprising from 2 to 50 alkylene, in particular ethylene, oxide groups, and mixtures thereof.

The anionic surfactants comprising a carboxyl group are particularly preferred.

(ii) Nonionic Surfactant(s)

The nonionic surface-active agents themselves are also compounds which are well known per se (in this respect see especially the "Handbook of Surfactants" by M. R. Porter, published by Blackie & Son (Glasgow and London), 1991, pp. 116–178, the disclosure of which is incorporated by reference) and, in the context of the present invention, their nature does not assume any critical character. They can thus be chosen especially from (nonlimiting list) alcohols, alphadiols, alkylphenols or polyethoxylated, polypropoxylated or polyglycerolated fatty acids which have a fatty chain containing, for example, 8 to 18 carbon atoms, it being generally possible for the number of ethylene oxide or propylene oxide groups to range especially from 2 to 50 and it being more particularly possible for the number of glycerol groups to range especially from 2 to 30. The copolymers of ethylene oxide and propylene oxide and the condensates of ethylene oxide and propylene oxide with fatty alcohols may also be mentioned; the polyethoxylated fatty amides preferably containing from 2 to 30 moles of ethylene oxide, the polyglycerolated fatty amides containing on average 1 to 5 glycerol groups and in particular 1.5 to 4; the polyethoxylated fatty amines preferably containing 2 to 30 moles of ethylene oxide; the oxyethylenated fatty acid esters of sorbitan containing from 2 to 30 moles of ethylene oxide; the fatty acid esters of sucrose, the esters of polyethylene glycol, alkylpolyglycosides, the N-alkylglucamine derivatives, amine oxides such as the oxides of ($C_{10}$–$C_{14}$)-alkylamines or the N-acylaminopropylmorpholine oxides. It will be noted that alkylpolyglycosides constitute nonionic surfactants which are particularly well suited within the context of the present invention.

(iii) Amphoteric or Zwitterionic Surfactant(s)

The amphoteric or zwitterionic surfactants, the nature of which is not of critical importance in the context of the present invention, may be especially (nonlimiting list) derivatives of aliphatic secondary or tertiary amines in which the aliphatic radical is a linear or branched chain containing 8 to 18 carbon atoms and containing at least one water-solubilizing anionic group (for example carboxylate, sulphonate, sulphate, phosphate or phosphonate); ($C_8$–$C_{20}$) alkylbetaines, sulphobetaines, ($C_8$–$C_{20}$)alkylamido($C_1$–$C_6$) alkylbetaines or ($C_8$–$C_{20}$)alkylamido($C_1$–$C_6$) alkylsulphobetaines may further be mentioned.

Among the amine derivatives, there may be mentioned the products sold under the name MIRANOL, as described in U.S. Pat. Nos. 2,528,378 and 2,781,354 and classified in the CTFA dictionary, $3^{rd}$ edition, 1982, the disclosures of which are incorporated by reference, under the names Amphocarboxyglycinates and Amphocarboxypropionates having the respective structures:

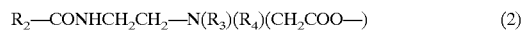

$R_2$—CONHCH$_2$CH$_2$—N($R_3$)($R_4$)(CH$_2$COO—)    (2)

in which: $R_2$ is an alkyl, preferably, an alkyl radical of an acid $R_2$—COOH present in hydrolysed copra oil, or a heptyl, nonyl or undecyl radical; $R_3$ is a beta-hydroxyethyl group; and $R_4$ is a carboxymethyl group; and

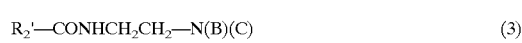

$R_2'$—CONHCH$_2$CH$_2$—N(B)(C)    (3)

in which:
B is —CH$_2$CH$_2$OX', C is —(CH$_2$)$_z$—Y', with z being 1 or 2,
X' is a —CH$_2$CH$_2$—COOH group or a hydrogen atom,
Y' is —COOH or a —CH$_2$—CHOH—SO$_3$H radical,
$R_2'$ is an alkyl, preferably, an alkyl radical of an acid $R_2'$—COOH present in copra oil or in hydrolysed linseed oil, or a $C_7$, $C_9$, $C_{11}$ or $C_{13}$ alkyl radical, a $C_{17}$ alkyl radical, or a $C_{17}$ alkyl radical and its iso form, or an unsaturated $C_{17}$ radical.

These compounds are classified in the CTFA dictionary, 5th edition, 1993, the disclosure of which is incorporated by reference, under the names Disodium Cocoamphodiacetate, Disodium Lauroamphodiacetate, Disodium Caprylamphodiacetate, Disodium Caproamphodiacetate, Disodium Cocoamphodipropionate, Disodium Lauroamphodipropionate, Disodium Caprylamphodipropionate, Disodium Caproamphodipropionate, Lauroamphodipropionic acid, and Cocoamphodipropionic acid.

By way of example, there may be mentioned the cocoamphodiacetate marketed under the trade name MIRANOL® C2M concentrate by the company RHODIA CHIMIE.

In the compositions in accordance with the invention, mixtures of surfactants and in particular mixtures of anionic and amphoteric or nonionic surfactants are preferably used. A particularly preferred mixture is a mixture comprising at least one carboxylic anionic surfactant and at least one amphoteric or nonionic surfactant.

An anionic surfactant is preferably used which is chosen from polyoxyalkylenated ($C_6$–$C_{24}$)alkyl ether carboxylic acids, polyoxyalkylenated ($C_6$–$C_{24}$)alkylaryl ether carboxylic acids, polyoxyalkylenated ($C_6$–$C_{24}$)alkyl amidoether carboxylic acids and their mixture with a sulphonated or sulphated surfactant such as sodium, triethanolamine or ammonium ($C_{12}$–$C_{24}$)alkyl sulphates, oxyethylenated sodium ($C_{12}$–$C_{14}$)alkyl ether sulphates containing 2.2 mol of ethylene oxide, sodium cocoylisethionate and their mixtures with:

either an amphoteric surfactant such as the amine derivatives called disodium cocoamphodipropionate or sodium cocoamphopropionate marketed in particular by the company RHODIA CHIMIE under the trade name MIRANOL®

C2M CONC in aqueous solution containing 38% of active substance or under the name MIRANOL® C32;

a zwitterionic-type amphoteric surfactant such as the alkylbetaines in particular the cocobetaine marketed under the name DEHYTON® AB 30 in aqueous solution containing 32% AS by the company HENKEL or the alkylamidoalkylbetaines such as TEGOBETAINE®F50 marketed by the company GOLDSCHMIDT; or an alkyl polyglucoside-type nonionic surfactant.

(iv) Cationic Surfactants

Among the cationic surfactants, there may be mentioned in particular (nonlimiting list): the salts of optionally polyoxyalkylenated primary, secondary or tertiary amines; quaternary ammonium salts, such as tetraalkylammonium, alkylamidoalkyltrialkylammonium, trialkylbenzylammonium, trialkylhydroxyalkylammonium or alkylpyridinium chlorides or bromides; imidazoline derivatives or amine oxides of a cationic nature.

It will be noted that the cationic surfactants, whose use is not excluded, do not constitute preferred surfactants for carrying out the present invention.

B—Silicone(s)

The compositions in accordance with the invention comprise, in addition, at least one water-insoluble silicone.

The silicones which can be used in accordance with the invention may be in particular polyorganosiloxanes which are insoluble in the composition. These silicones may be provided in the form of oils, waxes, resins or gums.

The viscosity of the silicones is measured at 25° C. according to the ASTM 445 Annex C standard.

The water-insoluble silicones are insoluble in water at a concentration greater than or equal to 0.1% by weight in water at 25° C., that is to say that they do not form a transparent isotropic solution.

The organopolysiloxanes are defined in greater detail in the book by Walter NOLL, "Chemistry and Technology of Silicones", (1968), Academic Press, the disclosure of which is incorporated by reference.

Preferably used are nonvolatile silicones and more particularly
(i) polyalkylsiloxanes;
(ii) polyarylsiloxanes;
(iii) polyalkylarylsiloxanes;
(iv) silicone gums;
(v) silicone resins; or
(vi) mixtures thereof.

The polyalkylsiloxanes preferably have a viscosity greater than or equal to 500 cSt and less than 1,000,000, more particularly ranging from 10,000 to 700,000 cSt. Among the polyalkylsiloxanes, there may be mentioned mainly:

linear polydimethylsiloxanes with terminal trimethylsilyl groups, such as for example, and without limitation, the SILBIONE® oils of the 70047 series which are marketed by RHODIA CHIMIE, the SILBIONE® 47 V 500000 oil from RHODIA CHIMIE or some types of VISCASIL from GENERAL ELECTRIC; and linear polydimethylsiloxanes with terminal hydroxydimethylsilyl groups such as the oils of the 48 V series from RHODIA CHIMIE.

In this class of polyalkylsiloxanes, there may also be mentioned the polyalkylsiloxanes sold by the company GOLDSCHMIDT under the trade names ABILWAX® 9800 and ABILWAX® 9801 which are poly($C_1$–$C_{20}$) alkylsiloxanes.

Among the polyalkylarylsiloxanes, there may be mentioned the linear or branched polydimethylmethylphenylsiloxanes or polydimethyldiphenylsiloxanes such as the product DC 556 COSMETIC GRAD FLUID from DOW CORNING.

The silicone gums in accordance with the invention may be polyorganosiloxanes having a number-average molecular mass ranging from 200,000 to 1,000,000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane, tridecanes and mixtures thereof.

The following compounds may be mentioned for example:
polydimethylsiloxane,
poly((dimethylsiloxane)/(methylvinylsiloxane)),
poly((dimethylsiloxane)/(diphenylsiloxane)),
poly((dimethylsiloxane)/(phenylmethylsiloxane)), and
poly((dimethylsiloxane)/(diphenylsiloxane)/(methylvinylsiloxane)).

The following mixtures may be mentioned for example:

1) mixtures formed from a polydimethylsiloxane, which is hydroxylated at the end of the chain (DIMETHICONOL according to the CTFA nomenclature), and from a cyclic polydimethylsiloxane (CYCLOMETHICONE according to the CTFA nomenclature), such as the product Q2 1401 sold by the company DOW CORNING;

2) mixtures formed from a polydimethylsiloxane gum with a cyclic silicone, such as the product SF 1214 SILICONE FLUID from GENERAL ELECTRIC, which is an SE 30 gum having a molecular weight of 500,000, solubilized in SF 1202 SILICONE FLUID (decamethylcyclopentasiloxane);

3) mixtures of two polydimethylsiloxanes (PDMS) of different viscosity, in particular of a PDMS gum and a PDMS oil, such as the products SF 1236 and CF 1241 from GENERAL ELECTRIC. The product SF 1236 is a mixture of an SE 30 oil defined above, having a viscosity of 20 $m^2$/s, and an SF 96 oil having a viscosity of $5.10^{-5}$ $m^2$/s (15% of SE 30 gum and 85% of SF 96 oil). The product CF 1241 is the mixture of an SE 30 gum (33%) and a PDMS (67%) having a viscosity of $10^{-3}$ $m^2$/s.

The silicone resins in accordance with the invention are preferably crosslinked siloxane systems containing the units: $R_2SiO_{2/2}$, $RSiO_{3/2}$, $SiO_{4/2}$, in which R is a hydrocarbon group possessing from 1 to 6 carbon atoms or a phenyl group. Among these products, those particularly preferred are those where R is a lower alkyl or phenyl radical.

Among these silicone resins, there may be mentioned the product sold under the name DOW CORNING 593 by DOW CORNING or those sold under the name SILICONE FLUID SS 4267 by GENERAL ELECTRIC and which are dimethyl/trimethylpolysiloxanes.

According to the invention, the silicones may also be used in the form of emulsions or microemulsions.

The particularly preferred silicones in accordance with the invention are:

silicones chosen from polydimethylsiloxanes with terminal trimethylsilyl groups such as the oils having a viscosity of from 0.2 to 2.5 $m^2$/s at 25° C., such as the oils of the DC200 series from DOW CORNING, in particular the one having a viscosity of 60,000 cSt, of the SILBIONE® 70047 and 47 series, and more particularly the SILBIONE® 70 047 V 500 000 oil marketed by the company RHODIA CHIMIE, or the silicone oil AK 300.000 from the company WACKER, the polydimethylsiloxanes containing terminal dimethylsilanol groups such as dimethiconol;

mixtures of organopolysiloxanes and cyclic silicones such as the product Q2 1401 marketed by the company DOW CORNING, and the product SF 1214 marketed by the company GENERAL ELECTRIC;

mixtures of two PDMSs of different viscosities, in particular of a gum and an oil such as the product SF 1236 marketed by the company GENERAL ELECTRIC; and an organopolysiloxane resin marketed under the name DOW CORNING 593.

According to the invention, the silicone(s) may be present in the composition in an amount ranging from 0.001% to 10% by weight, preferably from 0.005% to 5% by weight, and still more preferably from 0.01% to 3% by weight relative to the total weight of the final composition.

C—Amphoteric Polymers Comprising at Least One Fatty Chain

The detergent, in particular hair, compositions in accordance with the invention, may contain, in addition, at least one amphoteric polymer comprising at least one fatty chain.

The amphoteric polymers according to the invention comprise from 1 to 20 mol % of the monomeric units comprising a fatty chain, and preferably from 1.5 to 15 mol % and still more particularly from 1.5 to 6 mol % relative to the total number of moles of monomeric units in the polymers.

The amphoteric polymers according to the invention may result from the copolymerization 1) of at least one monomer chosen from (meth)acrylate and (meth)acrylamide types of formula (Ia) and (Ib):

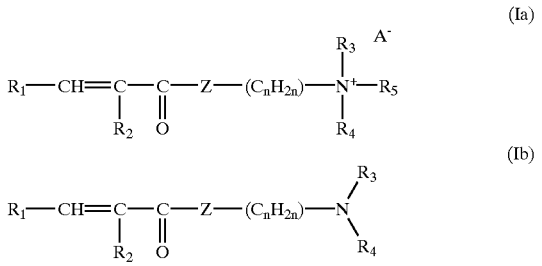

in which:

$R_1$ and $R_2$, which are identical or different, are a hydrogen atom or a methyl radical; $R_3$, $R_4$ and $R_5$, which are identical or different, are chosen from linear and branched alkyl radicals having from 1 to 30 carbon atoms;

Z is an NH group or an oxygen atom;

n is an integer ranging from 2 to 5; and $A^-$ is an anion derived from an organic or inorganic acid, such as a methosulphate anion or a halide, such as chloride or bromide;

2) of at least one monomer chosen from (meth)acrylate and (meth)acrylamide types of formula (II)

in which: $R_6$ and $R_7$, which are identical or different, are a hydrogen atom or a methyl radical; and 3) of at least one monomer chosen from (meth)acrylate and (meth)acrylamide types of formula (III):

in which: $R_6$ and $R_7$, which are identical or different, are a hydrogen atom or a methyl radical; X is an oxygen or nitrogen atom; and $R_8$ is chosen from linear and branched alkyl radicals having from 1 to 30 carbon atoms;

at least one of the (meth)acrylate and (meth)acrylamide type of monomers of formula (Ia), (Ib) or (III) comprises at least one fatty chain having from 8 to 30 carbon atoms.

The monomers of formula (Ia) and (Ib) of the present invention are preferably chosen from:

dimethylaminoethyl methacrylate, dimethylaminoethyl acrylate, diethylaminoethyl methacrylate, diethylaminoethyl acrylate, dimethylaminopropyl methacrylate, dimethylamino-propyl acrylate, and dimethylaminopropylmethacrylamide, dimethylamino-propylacrylamide, these monomers being optionally quaternized, for example, with a $(C_1$–$C_4)$ alkyl halide or a $(C_1$–$C_4)$ dialkyl sulphate.

More particularly, the monomer of formula (Ia) is chosen from acrylamidopropyltrimethylammonium chloride and methacrylamidopropyltrimethylammonium chloride.

The monomers of formula (II) of the present invention are preferably chosen from acrylic acid, methacrylic acid, crotonic acid and 2-methylcrotonic acid.

More particularly, the monomer of formula (II) is acrylic acid.

The monomers of formula (III) of the present invention are preferably chosen from $(C_{12}$–$C_{22})$, and more particularly $(C_{16}$–$C_{18})$, alkyl acrylates and methacrylates.

The monomeric units constituting the amphoteric polymers of the invention are preferably already neutralized and/or quaternized.

The ratio of the number of cationic charges/anionic charges is preferably equal to about 1.

The weight-average molecular weights of the amphoteric polymers according to the invention can range from 500 to 50,000,000 and are preferably range from 10,000 to 5,000,000.

Polymers according to the invention may also contain other monomers, such as nonionic monomers and in particular, such as $(C_1$–$C_4)$ alkyl acrylates or methacrylates.

Amphoteric polymers according to the invention are in particular described in patent application WO 98/44012, the disclosure of which is incorporated by reference.

The particularly preferred amphoteric polymers according to the invention are chosen from acrylic acid/acrylamidopropyltrimethylammonium chloride/stearyl methacrylate copolymers.

The amphoteric polymer is preferably used in the composition in an amount ranging from 0.05 to 10% by weight relative to the total weight of the composition. More preferably, this amount is from 0.1 to 5% by weight relative to the total weight of the composition.

The cosmetically acceptable aqueous medium can be solely water or a mixture of water and a cosmetically acceptable solvent such as a lower $(C_1$–$C_4)$ alcohol, such as ethanol, isopropanol, tert-butanol or n-butanol; alkylene glycols such as propylene glycol or glycol ethers. Preferably, the composition comprises from 50 to 95% by weight of water relative to the total weight of the composition.

The detergent compositions according to the invention have a final pH generally ranging from 3 to 10. Preferably, the pH ranges from 4 to 9. The adjustment of the pH to the desired value may be carried out conventionally by addition of a base (organic or inorganic) to the composition, for example ammonium hydroxide or a primary, secondary or tertiary (poly)amine, such as monoethanolamine, diethanolamine, triethanolamine, isopropanolamine or 1,3-propanediamine, or by the addition of an inorganic or organic acid, preferably a carboxylic acid, such as, for example citric acid.

The compositions in accordance with the invention may also contain viscosity-regulating agents such as electrolytes, or thickening agents. There may be mentioned in particular sodium chloride, sodium xylenesulphonate, scleroglucans, xanthan gums, fatty acid alkanolamides, alkyl ether carboxylic acid alkanolamides which are optionally oxyethylenated with up to 5 mol of ethylene oxide, such as the product marketed under the name AMINOL A15 by the company CHEM Y, crosslinked polyacrylic acids and crosslinked acrylic acidl($C_{10}$–$C_{30}$) alkyl acrylate copolymers. These viscosity-regulating agents are used in the compositions according to the invention in proportions which may be up to 10% by weight relative to the total weight of the composition.

The compositions in accordance with the invention may also contain up to 5% of pearlescent or opacifying agents which are well known in the state of the art, such as, for example ($C_{16}$) higher fatty alcohols, sodium palmitates, magnesium palmitates, sodium stearates, magnesium stearates and hydroxystearates, fatty chain-containing acylated derivatives, such as ethylene glycol or polyethylene glycol monostearates or distearates, fatty chain-containing ethers such as, for example, distearyl ether or 1-(hexadecyloxy)-2-octadecanol.

The detergent compositions according to the invention may of course contain, in addition, all the customary adjuvants encountered in the field of shampoos, such as for example perfumes, preservatives, sequestrants, thickeners, softeners, foam modifiers, colorants, pearlescent agents, moisturizing agents, antidandruff agents, antiseborrhoeic agents, sunscreens and the like.

The compositions in accordance with the invention may also optionally contain other agents which have the effect of improving the cosmetic properties of hair or skin without, however, adversely impairing the stability of the compositions. There may be mentioned, in this respect, cationic surfactants, anionic or nonionic and more particularly cationic polymers, amphoteric polymers other than those of the invention, proteins, protein hydrolysates, ceramides, pseudoceramides, fatty acids with linear or branched ($C_{16}$–$C_{40}$) chains such as 18-methyleicosanoic acid, hydroxy acids, vitamins, panthenol, silicones, which are volatile or nonvolatile, soluble or insoluble in the medium, vegetable oils, synthetic oils and mixtures thereof.

The compositions according to the invention preferably comprise one or more cationic polymers. The cationic polymers which can be used in accordance with the present invention may be chosen from all those already known per se to improve the cosmetic properties of hair treated with detergent compositions, namely in particular those described in Patent Application EP-A-0,337,354 and in French Patent Applications FR-A-2,270,846; 2,383,660; 2,598,611; 2,470,596 and 2,519,863, the disclosures of which are incorporated by reference.

Still more generally, for the purposes of the present invention, the expression "cationic polymer" denotes any polymer containing cationic groups and/or groups which are ionized into cationic groups.

Among all the cationic polymers which can be used in the context of the present invention, it is preferable to use quaternary cellulose ether derivatives such as the products marketed under the name JR 400 by the company UNION CARBIDE CORPORATION, cyclopolymers, in particular homopolymers of the salt of diallyldimethylammonium and the copolymers of the salt of diallyldimethylammonium and of acrylamide, in particular the chlorides, marketed under the names MERQUAT 100, MERQUAT 550 and MERQUAT S by the company MERCK, cationic polysaccharides and more particularly the guar gums modified by 2,3-epoxypropyltrimethylammonium chloride which are marketed, for example, under the name JAGUAR C13S by the company MEYHALL, the vinylpyrrolidone/methacrylamidopropyldimethylamine copolymers and mixtures thereof.

According to the invention, the cationic polymer(s) may represent from 0.001% to 10% by weight, preferably from 0.005% to 5% by weight, and still more preferably from 0.01% to 3% by weight, of the total weight of the final composition.

The compositions according to the invention may also contain foam synergists such as ($C_{10}$–$C_{18}$) 1,2-alkanediols or fatty alkanolamides derived from monoethanolamine or diethanolamine.

Of course, persons skilled in the art will be careful to choose this or these possible additional compounds and/or their quantities such that the advantageous properties intrinsically attached to the combination in accordance with the invention are not, or are not substantially, adversely impaired by the addition(s) envisaged.

These compositions may be provided in the form of more or less thickened liquids, creams or gels and they are mainly suitable for the washing, caring for and/or styling the hair.

The compositions of the invention may also be provided in the form of washing compositions for the skin, and in particular in the form of bath or shower solutions or gels or make-up removing products.

When the compositions in accordance with the invention are used as conventional shampoos, they are simply applied to the keratinous materials, in particular dry, or preferably wet, hair and the foam generated by massaging or rubbing with the hands is then removed after optionally leaving it to stand on the hair for a certain amount of time, by rinsing, preferably with water, it being possible for the operation to be repeated once or several times.

The subject of the invention is also a process for washing and conditioning keratinous materials comprising applying to the dry or wet materials an effective amount of a composition as defined above, and then in rinsing with water after optionally leaving it to stand on the hair for a certain amount of time.

Concrete examples illustrating the invention, but which are not at all limiting, will now be given.

EXAMPLE 1

Two shampoo compositions, one in accordance with the invention (composition A) and the other comparative (composition B), differing from each other simply in the nature of the amphoteric polymer used, were prepared:

|  | A | B |
|---|---|---|
| Sodium lauryl ether sulphate (2.2 EO) | 15.4 g AS | 15.4 g AS |
| Sodium cocoamphocarboxyglycinate (MIRANOL C2M Conc from RHODIA CHIMIE) | 3 g AS | 3 g AS |

-continued

|  | A | B |
|---|---|---|
| Polydimethylsiloxane having a viscosity of 500,000 cSt (MIRASIL DM 500.000 from RHODIA CHIMIE) | 2.7 g | 2.7 g |
| Terpolymer of methacrylamidopropyl-trimethylammonium chloride, acrylic acid and stearyl methacrylate (49/49/2 mol %) | 0.5 g AS | |
| Terpolymer of methacrylamidopropyl-trimethylammonium chloride, acrylic acid (50/50 mol %) | | 0.5 g AS |
| 1-(Hexadecyloxy)-2-octadecanol/cetyl alcohol | 2.5 | 2.5 |
| Preservative | q.s | q.s |
| pH adjusted to | 7 | 7 |
| Water qs | 100 g | 100 g |

Locks of 2.5 g of natural hair 27 cm long were wetted beforehand and then brought into contact with 1 g of composition A according to the invention for 5 minutes and then rinsed with water. The locks were then dried under a hood dryer for 20 minutes at 65° C. The procedure was carried out according to the same procedure as above with the comparative composition B.

Evaluation of the Feel of the Locks

The locks prepared as indicated above were presented to a panel of 10 testers. They were asked to indicate the locks which they judge to be softer and sleeker.

The 10 judges were unanimous and declared that the hair treated with composition A was softer and sleeker.

What is claimed is:

1. A detergent composition comprising, at least one washing base, at least one water-insoluble silicone and at least one amphoteric polymer comprising from 1 to 20 mol % of at least one monomeric unit chosen from (meth)acrylate and (meth)acrylamide having at least one fatty chain, the fatty chain having from 8 to 30 carbon atoms.

2. The composition according to claim 1, wherein the composition further comprises a cosmetically acceptable medium.

3. The composition according to claim 1, wherein the at least one washing base comprises at least one surfactant chosen from anionic, amphoteric, nonionic and zwitterionic surfactants.

4. The composition according to claim 1, wherein the at least one washing base is present in the composition in an amount ranging from 4% to 50% by weight relative to the total weight of the composition.

5. The composition according to claim 4, wherein the at least one washing base is present in the composition in an amount ranging from 6% to 25% by weight relative to the total weight of the composition.

6. The composition according to claim 1, wherein the at least one amphoteric polymer comprises from 1.5 to 15 mol % of monomeric units comprising a fatty chain relative to the total number of moles of monomeric units in said at least one polymer.

7. The composition according to claim 6, wherein the at least one amphoteric polymer comprises from 1.5 to 6 mol % of monomeric units comprising a fatty chain relative to the total number of moles of monomeric units in said at least one polymer.

8. The composition according to claim 1, wherein the at least one amphoteric polymer results from copolymerization 1) of at least one monomer chosen from (meth)acrylate and (meth)acrylamide of formula (Ia) and (Ib):

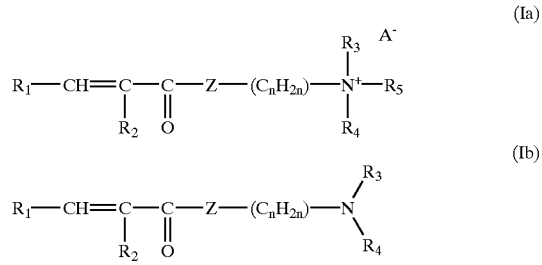

in which:
R$_1$ and R$_2$, which are identical or different, are a hydrogen atom or a methyl radical; R$_3$, R$_4$ and R$_5$, which are identical or different, are chosen from linear and branched alkyl radicals having from 1 to 30 carbon atoms;
Z is an NH group or an oxygen atom;
n is an integer ranging from 2 to 5, and
A$^-$ is an anion derived from an organic or inorganic acid;

2) of at least one monomer chosen from (meth)acrylate and (meth)acrylamide of formula (II)

in which:
R$_6$ and R$_7$, which are identical or different, are a hydrogen atom or a methyl radical;
and 3) of at least one monomer chosen from (meth)acrylate and (meth)acrylamide of formula (III):

in which: R$_6$ and R$_7$, which are identical or different, are a hydrogen atom or a methyl radical; X is an oxygen or nitrogen atom; and R$_8$ is chosen from linear and branched alkyl radicals having from 1 to 30 carbon atoms;
wherein at least one of the (meth)acrylate and (meth)acrylamide of monomers of formula (Ia), (Ib) or (III) comprises at least one fatty chain having from 8 to 30 carbon atoms.

9. The composition according to claim 8, wherein the at least one monomer of formula (Ia) and (Ib) is chosen from:
dimethylaminoethyl methacrylate, dimethylaminoethyl acrylate,
diethylaminoethyl methacrylate, diethylaminoethyl acrylate,
dimethylaminopropyl methacrylate, dimethylaminopropyl acrylate, and
dimethylaminopropylmethacrylamide, dimethylaminopropylacrylamide, these monomers being optionally quaternized.

10. The composition according to claim 8, wherein the at least one monomer of formula (Ia) is chosen from acrylamidopropyltrimethyl-ammonium chloride and methacrylamidopropyltrimethyl-ammonium chloride.

11. The composition according to claims 8, wherein the at least one monomer of formula (II) is chosen from acrylic acid, methacrylic acid, crotonic acid and 2-methylcrotonic acid.

12. The composition according to claim 8, wherein the at least one monomer of formula (III) is chosen from (C$_{12}$–C$_{22}$), alkyl acrylates and methacrylates.

13. The composition according to claim 12, wherein the at least one monomer of formula (III) is chosen from ($C_{12}$–$C_{22}$) alkyl acrylates and methacrylates.

14. The composition according to claim 1, wherein the at least one amphoteric polymer is chosen from acrylic acid/ acrylamidopropyltrimethylammonium chloride/stearyl methacrylate copolymers.

15. The composition according to claim 1, wherein the at least one amphoteric polymer is present in the composition in an amount ranging from 0.05 to 10% by weight relative to the total weight of the composition.

16. The composition according to claim 1, wherein the at least one water-insoluble silicone is chosen from:

(i) polyalkylsiloxanes;

(ii) polyarylsiloxanes;

(iii) polyalkylarylsiloxanes;

(iv) silicone gums; and (v) silicone resins.

17. The composition according to claim 1, wherein the at least one water-insoluble silicone is chosen from:

polydimethylsiloxanes with terminal trimethylsilyl groups, and polydimethylsiloxanes with terminal dimethylsilanol groups.

18. The composition according to claim 1, wherein the at least one water-insoluble silicone is present in the composition in an amount ranging from 0.01% to 10% by weight relative to the total weight of the composition.

19. The composition according to claim 18, wherein the least one water-insoluble silicone is present in the composition in an amount ranging from 0.05% to 5% by weight relative to the total weight of the composition.

20. The composition according to claim 1, wherein the composition also comprises at least one additive chosen from cationic surfactants, anionic polymers, nonionic polymers, cationic polymers, amphoteric polymers differing from said at least one amphoteric polymer, proteins, protein hydrolysates, ceramides, pseudoceramides, fatty acids containing linear ($C_{16}$–$C_{40}$) chains, fatty acids containing branched ($C_{16}$–$C_{40}$) chains, hydroxy acids, vitamins, panthenol, volatile silicones, nonvolatile silicones which are soluble in the medium, nonvolatile silicones which are insoluble in the medium, vegetable oils, and synthetic oils.

21. The composition according to claim 20, wherein said at least one additive is 18-methyleicosandic acid.

22. The composition according to claim 20, wherein the cationic polymers are chosen from quaternary cellulose ether derivatives, cyclopolymers, cationic polysaccharides, and vinylpyrrolidone/methacrylamidopropyidimethylamine copolymers.

23. The composition according to claim 1, wherein the composition has a pH ranging from 4 to 9.

24. A method for cleaning, caring for, conditioning, or styling hair comprising applying to the hair a composition comprising, at least one washing base, at least one water-insoluble silicone and at least one amphoteric polymer comprising from 1 to 20 mol % of at least one monomeric unit chosen from (meth)acrylate and (meth)acrylamide having at least one fatty chain, the fatty chain having from 8 to 30 carbon atoms.

25. A process for washing and conditioning a keratinous material comprising applying to a keratinous material an effective amount of a composition comprising at least one washing base, at least one water-insoluble silicone and at least one amphoteric polymer comprising from 1 to 20 mol % of at least one monomeric unit chosen from (meth) acrylate and (meth)acrylamide having at least one fatty chain, the fatty chain having from 8 to 30 carbon atoms, and rinsing the substance with water after optionally leaving the composition to stand on the substance for a certain amount of time, wherein the substance is dry or wet.

* * * * *

UNITED STATES PATENT AND TRADEMARK OFFICE
CERTIFICATE OF CORRECTION

PATENT NO.     : 6,511,671 B1
DATED          : January 28, 2003
INVENTOR(S)    : Claude Dubief et al.

It is certified that error appears in the above-identified patent and that said Letters Patent is hereby corrected as shown below:

<u>Column 14,</u>
Line 13, "vinylpyrrolidone/methacrylamidopropyidimethylamine" should read
-- vinylpyrrolidone/methacrylamidopropyldimethylamine --.

Signed and Sealed this

Fifth Day of August, 2003

JAMES E. ROGAN
*Director of the United States Patent and Trademark Office*